United States Patent [19]

Turner et al.

[11] Patent Number: 5,365,072
[45] Date of Patent: Nov. 15, 1994

[54] REPOSITIONABLE SUBSTRATE FOR MICROSCOPES

[75] Inventors: David C. Turner, Alexandria, Va.; Bruce P. Gaber, Bethesda, Md.

[73] Assignee: The United States of America as represented by the Secretary of the Navy, Washington, D.C.

[21] Appl. No.: 113,126

[22] Filed: Aug. 30, 1993

[51] Int. Cl.$^5$ .............................................. H01J 37/20
[52] U.S. Cl. .................................................. 250/491.1
[58] Field of Search ...................................... 250/491.1

[56] References Cited

U.S. PATENT DOCUMENTS 4,370,554 1/1983 Bohlen et al. ..................... 250/491.1
5,117,110 5/1992 Yasutake ........................... 250/491.1

OTHER PUBLICATIONS

Yasutake et al., "Scanning tunneling microscope combined with optical microscope for large sample measurement", J. Vacuum Sci. Tech. A 8 (1) 350–53 (Jan./Feb. 1990).
McCord et al., "Lithography with the scanning tunneling microscope", J. Vacuum Sci. Tech. B 4 (1) 86–88 (Jan./Feb. 1986).
Putnam et al., "Atomic force microscope with integrated optical microscope for biological applications", Rev. Sci. Instrum. 63 (3) 1914–17 (Mar. 1992).
Ehrichs et al., "A scanning tunneling microscope/scanning electron microscope system for the fabrication of nanostructures", J. Vacuum Sci. Tech. B 9 (2) 1380–83 (Mar./Apr. 1991).
"MRS-2: Finally, a Magnification Reference Standard Designed for Microscopy by Microscopists . . . ", Geller Microanalytical Laboratory, One Intercontinental Way, Peabody, Massachusetts 01960.

*Primary Examiner*—Jack I. Berman
*Attorney, Agent, or Firm*—Thomas E. McDonnell; John J. Karasek

[57] ABSTRACT

The present invention is a repositionable substrate for microscope applications, having a geometric pattern on its top surface to convey coordinate information. In a preferred embodiment, this geometric pattern is a plurality of geometric shapes having a common axis of symmetry. In a most preferred embodiment, these geometric shapes are concentric, with varying linewidth.

8 Claims, 4 Drawing Sheets

REPOSITIONABLE SUBSTRATE FOR MICROSCOPES

BACKGROUND OF THE INVENTION

Field of the Invention

The present invention relates to substrates for microscopy, and more particularly to repositionable substrates for microscopic applications.

Description of the Related Art

One of the disadvantages of the scanning probe microscopes (which include such devices as atomic force microscopes and scanning tunnelling microscopes) is their very small field of view. Consequently, it is difficult to relocate a work area on a substrate once this work area is moved out of the field of view (i.e. away from the tip).

It is therefore desired to develop a way to reposition a work area on a substrate at the tip of a scanning probe microscope. One approach to this problem has been to integrate another microscope, such as an optical or an electron microscope, into the scanning probe microscope to provide images of the substrate and the tip. See, e.g., Yasutake et al., "Scanning tunnelling microscope combined with optical microscope for large sample measurement", J. Vacuum Sci. Tech. A 8 (1) 350-53 (Jan/Feb 1990) and McCord et al., "Lithography with the scanning tunnelling microscope", J. Vacuum Sci. Tech. B 4 (1) 86-88 (Jan/Feb 1986). This approach adds to the complexity of the apparatus. Moreover, there are other drawbacks to using these large-field microscopes to position the sample. Electron microscopes operate under vacuum, a serious drawback for practitioners who wish to work with biological specimens. Optical microscopes work well for materials which are visible down to the 1-10 $\mu$m scale, but not for smaller objects. Moreover, it is difficult to configure an integrated optical-scanning probe microscope to image the point of contact of the tip and the substrate.

Coded substrates have been developed for these applications. For example, Yasutake et al. teaches the use of substrates 10 patterned with number pairs 12 to provide x,y coordinates for the substrate surface, as shown in FIG. 1. However, this type of substrate practically requires the use of an integrated large-field microscope, because it is time-consuming for a scanning probe microscope to image numerals and other symbols.

Other approaches use capacitive or interferometric sensor systems to precisely position a substrate relative to the scanning tip. These approaches provide a calibrated x,y positioner for accurate repositioning of the tip with respect to the substrate. However, it is questionable whether, using these approaches, the substrate can be removed from the scanning probe microscope head and then replaced in the head with great precision.

SUMMARY OF THE INVENTION

Accordingly, it is an object of this invention to make an improved repositionable substrate for scanning probe microscope applications.

It is a further object of this invention to make a repositionable substrate for microscopic applications that do not need to operate in a vacuum.

It is a further object of this invention to make a repositionable substrate for microscopic applications that may be removed from the microscope and replaced with high precision.

It is a further object of this invention to make a repositionable substrate for use with scanning probe microscopes that are not integrated with microscopes having larger fields of view.

These and additional objects of the invention are accomplished by the structures and processes hereinafter described.

The present invention is a repositionable substrate for microscope applications, having a geometric pattern on its top surface to convey coordinate information.

BRIEF DESCRIPTION OF THE DRAWINGS

A more complete appreciation of the invention will be readily obtained by reference to the following Description of the Preferred Embodiments and the accompanying drawings in which like numerals in different figures represent the same structures or elements, wherein.

DETAILED DESCRIPTION OF THE PREFERRED EMBODIMENTS

Figures 1, 2:
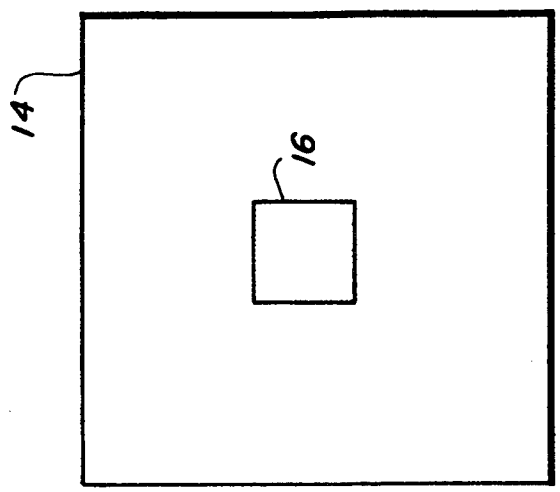
FIG. 1 is a top view detail of a known substrate pattern.
FIG. 2 is a top view of a preferred embodiment of the invention.

Referring to FIG. 2, a preferred repositionable substrate 14 according to the present invention has at least one patterned working region 16 on the substrate. This patterned working region 16 preferably is large enough to be readily positioned within the viewing area of the microscope. Preferably, this patterned region is large enough to be visible to the naked eye.

Figure 3:
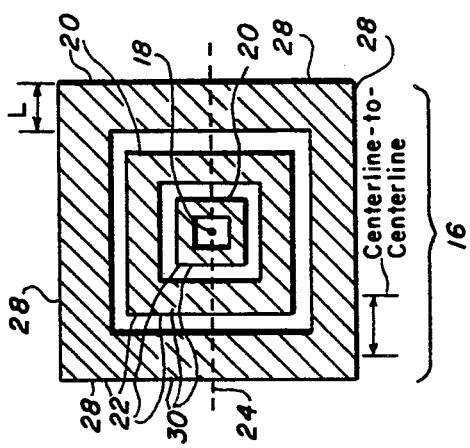
FIG. 3 is a top view detail of a preferred substrate pattern according to the invention.

As shown in, e.g., FIG. 3, this region of the substrate has a geometric pattern 20 for providing coordinate information that gives the position of the viewing region relative to a preselected origin point 18 on the substrate surface. From this information the origin point 18, or any other arbitrarily selected point on the substrate surface, may be readily located and the scanning tip of the microscope relocated to this position.

This geometric pattern 20 has characteristic sizes and shapes that provide this coordinate information. Thickness, linewidth, and orientation are some characteristic aspects of the geometric pattern that provide this coordinate information. Thus, this geometric pattern is distinguishable from symbols (such as numerals) which may provide coordinate information according to their value, rather than according to their characteristic sizes and shapes.

It is advantageous to use geometric patterns to provide coordinate information for substrates used in scanning probe microscopes, due to the peculiar characteristics of scanning probe microscopes. These microscopes work by moving a very fine probe (also referred to in the literature as a "tip") across a surface, and measuring the changes in some quantity (e.g. voltage or force) as the tip moves from point to point on the surface. Accordingly, these microscopes are adept at determining the dimensions (e.g. linewidth and line thickness) and orientation of simple geometric structures on the surface. However, imaging complex symbols (e.g. alphanumeric characters) is more difficult. This is the reverse of the situation encountered with optical and electron microscopes, where it is simple to read imaged symbols, but measuring certain dimensions (especially thickness) is difficult.

Figure 4:
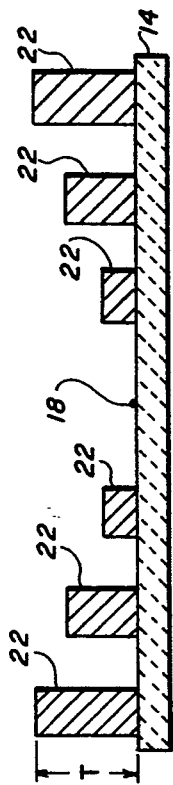
FIG. 4 is a side view of a preferred embodiment of the invention.
Figure 6:
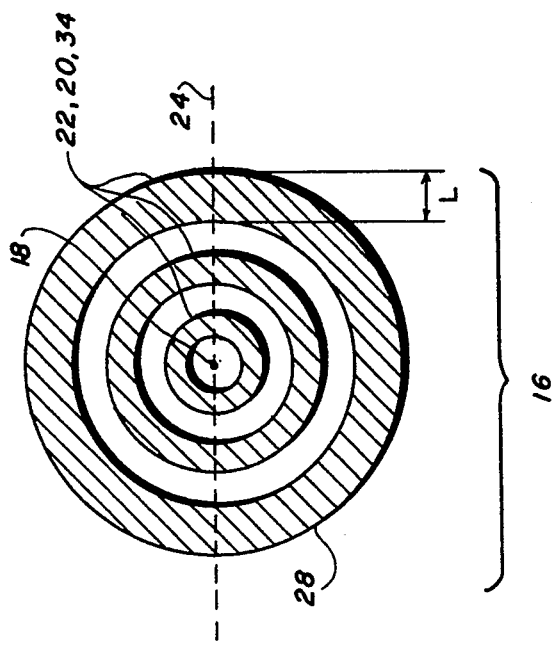
FIG. 6 is a top view detail of another preferred substrate pattern according to the invention.

Preferably, as shown in, e.g., FIG. 3, the geometric pattern 20 has a plurality of geometric shapes 22 having at least one common axis of symmetry passing through an origin point 18 on the substrate surface, where each of these geometric shapes has one or more lines 28 having a unique dimension (such as linewidth or line thickness) corresponding to a unique distance of the geometric shape from the origin point. FIG. 3 shows the linewidth corresponding to the distance from the origin point 18. Alternatively, as shown in FIG. 4, the line thickness (i.e., height) corresponds to the distance from the origin point 18. In a preferred embodiment, the geometric shapes 22 are concentric about the origin point 18.

Figure 5:
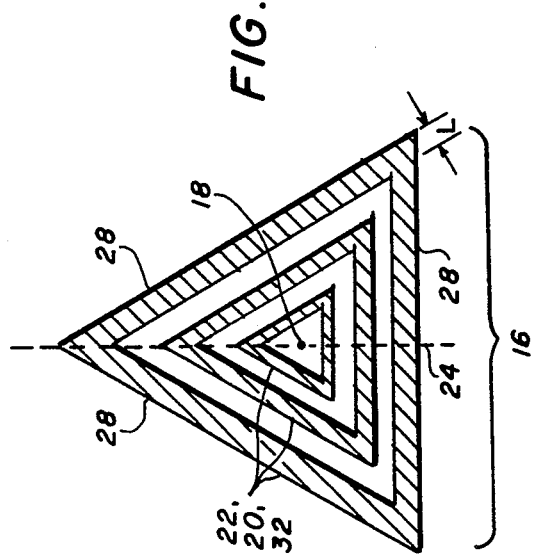
FIG. 5 is a top view detail of another preferred substrate pattern according to the invention.

The substrate may be patterned with a wide range of geometric shapes. As shown in FIGS. 3, 4, and 5, the substrate may be patterned with squares, triangles, and circles. Other geometric shapes may also be used.

Figure 7A:
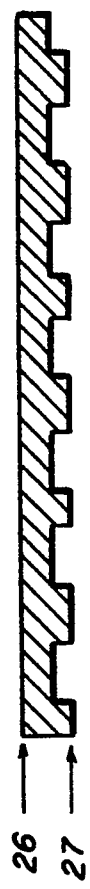
FIGS. 7A (top view), 7B (top view), and 7C (side view) shows several ways lines in a preferred substrate pattern may be contoured.
Figure 7B:
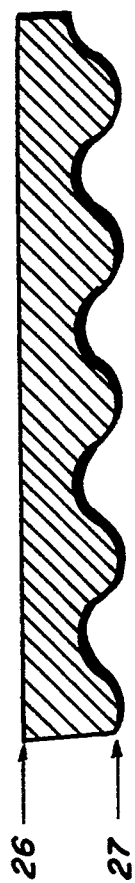
Figure 7C:
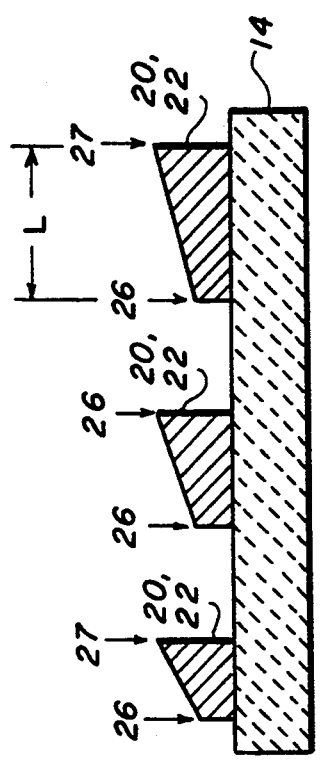

In a preferred embodiment, as shown in FIGS. 7A, 7B, and 7C, the edges 26,27 of the lines 28 making these geometric shapes 22 are contoured so that opposing edges 26,27 are distinguishable from each other by the scanning probe microscope. The edges may be contoured by, e.g., one of the edges 27 being notched (as shown in FIG. 7A), fluted (as shown in FIG. 7B), or a different thickness (as shown in FIG. 7C) than the opposing edge 26. This permits the operator to more readily distinguish one side of the line from another, thereby locating the origin point more easily.

Figure 8:
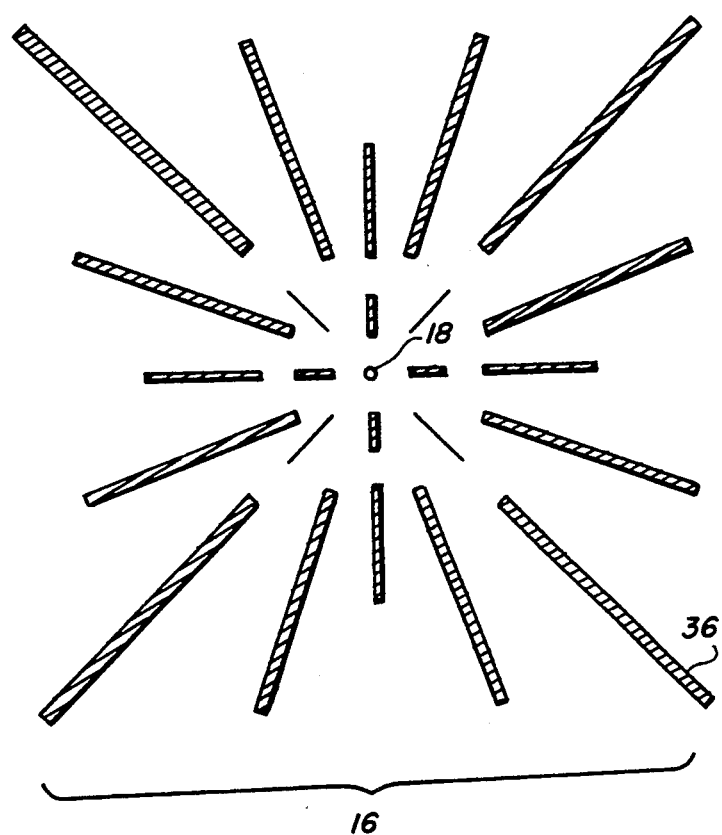
FIG. 8 is a top view detail of another preferred substrate pattern according to the invention.

In an alternative preferred embodiment, as shown in FIG. 8, the geometric pattern 20 may be a plurality of lines 36 indicating the direction of the origin point 18. In this embodiment, some dimension (e.g. linewidth, length, or thickness) of these lines will correspond to the distance to the origin. These lines in effect act as pointer arrows, pointing to the origin, with some dimension of the lines providing the distance to the origin.

Figure 9:
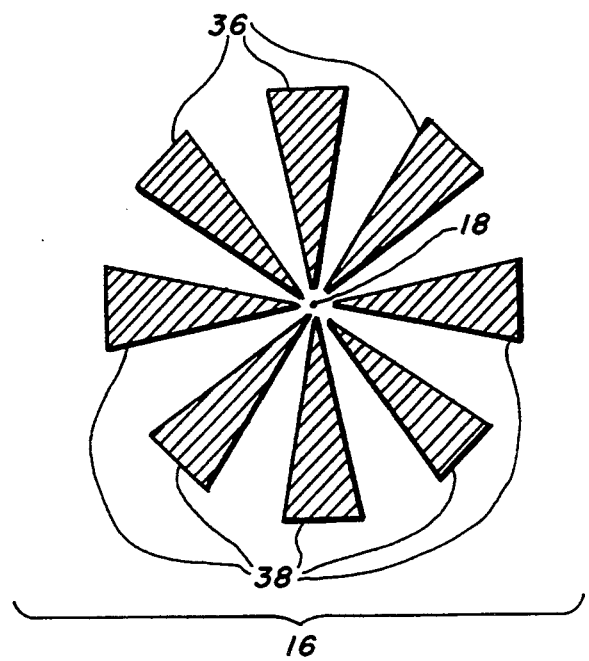
FIG. 9 is a top view detail of another preferred substrate pattern according to the invention.

In an alternative preferred embodiment, as shown in FIG. 9, the geometric pattern 20 may be a plurality of lines 38 arranged symmetrically about the origin point, where these lines vary in at least one dimension, e.g. linewidth, so that this variation corresponds to the distance to the origin point. For example, as shown in FIG. 9, the linewidth of each line varies linearly with the distance to the origin point.

In a most preferred embodiment, as shown in FIG. 3, the geometric pattern 20 comprises a plurality of concentric squares 30 centered about the origin 18. Preferably, the centerline-to-centerline spacing between adjacent concentric squares 30 is less than the width of the area imaged by the scanning probe head. Scanning probe heads are available in a wide range of sizes: 1 $\mu$m, 15 $\mu$m, 50 $\mu$m, 120 $\mu$m, etc. Selecting a centerline-to-centerline spacing between adjacent geometric shapes 22 that is less than the width of the area imaged by the scanning probe head assures that the operator can view the full width of any of the lines 28 making up the geometric pattern 20. This permits locating the origin, and consequently any other known point on the substrate, with only two translational movements of the tip.

In operation, the substrate is placed in the microscope, with the tip positioned anywhere in the patterned working region 16, and the surface pattern is observed, thereby conveying to the operator the position of the tip on the surface. The tip then can be moved to any arbitrarily selected position in the patterned working region 16. The substrate may be removed from the microscope, to optionally carry out desired processing steps. The substrate then can be returned to the microscope, with the tip positioned anywhere in the patterned working region 16. The surface pattern is observed again, thereby conveying to the operator the position of the tip on the surface. The tip then can be relocated to the previously selected position in the patterned working region, or optionally to some other region.

Having described the invention, the following examples are given to illustrate specific applications of the invention, including the best mode now known to perform the invention. These specific examples are not intended to limit the scope of the invention described in this application.

EXAMPLE 1:

A Substrate Patterned with Concentric Squares

A polished native silicon oxide substrate 14 was patterned with concentric Ni squares 30, using standard lithographic techniques. The edge length of the squares was $(2n-1) \times 12.0$ $\mu$m, and the linewidth of the squares was $(2n-1) \times 1.0$ $\mu$m, where n=1, 2, ... 12 is the number of a given square. Thus, each line was 1 $\mu$m wider than the preceding (towards the center) line. The lines were roughly 80 nm high. The overall pattern was about 300 $\mu$m across.

Lipid tubules were placed in the center of the pattern on the substrate. The substrate was placed in an atomic force microscope having a standard x,y translation stage. Care was taken to align the substrate square in the sample holder, and to position the AFM tip within the pattern on the substrate. The tip was put in contact with the substrate, and a vertical (i.e. parallel to the y-axis) nickel line was observed. The distance along the x-axis from the tip position to the x coordinate of the center of the pattern was calculated from the width of the nickel line. The tip was translated this calculated distance along the x-axis (i.e. to a point on the y-axis).

A horizontal nickel line was observed at the new tip position. The distance along the y-axis from the tip position to the y coordinate of the center of the pattern was calculated from the width of the nickel line. The tip was translated this calculated distance along the y-axis to the center of the pattern, where the lipid tubules were observed.

Obviously, many modifications and variations of the present invention are possible in light of the above teachings. It is therefore to be understood that, within the scope of the appended claims, the invention may be practiced otherwise than as specifically described.

What is claimed is:

1. A repositionable substrate for microscopic applications, comprising a substrate having a pattern on its top surface to convey coordinate information, wherein said pattern on said top surface comprises a plurality of concentric geometric shapes centered about an origin point on said top surface, wherein each of said plurality of said geometric shapes comprises one or more lines having a unique linewidth corresponding to a unique distance of said geometric shape from said origin point.

2. The repositionable substrate of claim 1, wherein each of said one or more lines having a unique linewidth has two opposing edges, wherein the first of said two opposing edges is contoured to be distinguishable from the second of said two opposing edges.

3. The repositionable substrate of claim 1, wherein said concentric geometric shapes are concentric squares.

4. The repositionable substrate of claim 1, wherein said concentric geometric shapes are concentric triangles.

5. The repositionable substrate of claim 1, wherein said concentric geometric shapes are concentric circles.

6. A repositionable substrate for microscopic applications, comprising a substrate having a pattern on its top surface to convey coordinate information, wherein said pattern on said top surface comprises a plurality of geometric shapes having at least one common axis of symmetry passing through an origin point on said top surface, wherein each of said plurality of said geometric shapes comprises one or more lines having a unique dimension corresponding to a unique distance of said geometric shape from said origin point.

7. A repositionable substrate for microscopic applications, comprising a substrate having a pattern on its top surface to convey coordinate information, wherein said pattern on said top surface comprises a plurality of geometric shapes having at least one common axis of symmetry passing through an origin point on said top surface, wherein each of said plurality of said geometric shapes varies in at least one dimension, wherein said variation in said dimension corresponds to a distance from said origin point.

8. A repositionable substrate for microscopic applications, comprising a substrate having a pattern on its top surface to convey coordinate information, wherein said pattern on said top surface comprises a plurality of lines, wherein the direction of each of said lines corresponds to the direction from said line to an origin point on said top surface, and wherein a physical dimension of each of said lines corresponds to the distance from said line to said origin point.

* * * * *